US009889265B2

(12) United States Patent
Fischer, Jr. et al.

(10) Patent No.: US 9,889,265 B2
(45) Date of Patent: *Feb. 13, 2018

(54) MANIFOLD HAVING ROTATABLE PORTS

(71) Applicant: Cook Medical Technologies LLC, Bloomington, IN (US)

(72) Inventors: Frank J. Fischer, Jr., Bloomingtom, IN (US); George A. Arndt, Madison, WI (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/423,319

(22) Filed: Feb. 2, 2017

(65) Prior Publication Data

US 2017/0143923 A1    May 25, 2017

Related U.S. Application Data

(63) Continuation of application No. 13/366,586, filed on Feb. 6, 2012, now Pat. No. 9,597,470.

(51) Int. Cl.
*A61M 15/00* (2006.01)
*A61M 16/00* (2006.01)
*A62B 9/00* (2006.01)
*A62B 18/00* (2006.01)
(Continued)

(52) U.S. Cl.
CPC ....... *A61M 16/0463* (2013.01); *A61B 1/2676* (2013.01); *A61M 16/0057* (2013.01); *A61M 16/0404* (2014.02)

(58) Field of Classification Search
None
See application file for complete search history.

(56) References Cited

U.S. PATENT DOCUMENTS 5,052,386 A    10/1991    Fischer, Jr.
5,250,038 A    10/1993    Melker et al.
(Continued)

FOREIGN PATENT DOCUMENTS

WO    WO 00/19013 A1    4/1999
WO    WO 2010/104393 A1    9/2010

OTHER PUBLICATIONS

Extended European Search Report dated Jul. 19, 2013 for European Patent Application No. EP 13153630.2, Munich, Germany, pp. 1-6.

*Primary Examiner* — Jacqueline Cheng
*Assistant Examiner* — Eric Bryant
(74) *Attorney, Agent, or Firm* — Brinks Gilson & Lione

(57) ABSTRACT

An airway manifold includes a manifold body having an upper body portion and a lower body portion. The body portions are engaged such that the upper body portion is rotatable relative to the lower body portion, whereby a generally hollow interior space is defined. The lower body portion has a port open to the interior space, and the upper body portion includes a plurality of ports open to the interior space. A first upper body port is axially alignable with the lower body port to define a substantially linear passageway therebetween when the upper body portion is at a first rotatable position relative to the lower body portion. A second upper body port is axially alignable with the lower body port to define a substantially linear passageway therebetween when the upper body portion is at a second rotatable position.

20 Claims, 7 Drawing Sheets

(51) Int. Cl.
*A61M 16/04* (2006.01)
*A61B 1/267* (2006.01)

(56) References Cited

U.S. PATENT DOCUMENTS

| | | | |
|---|---|---|---|
| 5,309,906 A * | 5/1994 | LaBombard | A61M 16/04 |
| | | | 128/207.14 |
| 5,322,513 A | 6/1994 | Walker | |
| 5,395,352 A * | 3/1995 | Penny | A61M 25/1025 |
| | | | 137/606 |
| 5,417,670 A | 5/1995 | Bottlik | |
| 5,711,294 A | 1/1998 | Kee et al. | |
| 5,713,849 A * | 2/1998 | Bosma | A61M 1/0084 |
| | | | 604/28 |
| 5,735,271 A | 4/1998 | Lorenzen et al. | |
| 5,803,078 A * | 9/1998 | Brauner | A61M 16/04 |
| | | | 128/200.14 |
| 5,904,648 A | 5/1999 | Arndt et al. | |
| 6,086,529 A | 7/2000 | Arndt | |
| 6,227,197 B1 | 5/2001 | Fitzgerald | |
| 6,328,730 B1 | 12/2001 | Harkrider, Jr. | |
| 6,363,273 B1 | 3/2002 | Mastrorio et al. | |
| 6,615,835 B1 | 9/2003 | Cise et al. | |
| 7,578,295 B2 | 8/2009 | Kurrus | |
| 2002/0078960 A1 | 6/2002 | Cise | |
| 2005/0268904 A1 | 12/2005 | Corey | |
| 2006/0090761 A1 | 5/2006 | Kurras | |
| 2007/0277828 A1 | 12/2007 | Ho et al. | |
| 2010/0147310 A1 | 6/2010 | Brewer et al. | |
| 2010/0163022 A1 | 7/2010 | Brewer et al. | |
| 2010/0163051 A1 | 7/2010 | Brewer et al. | |
| 2010/0288282 A1 | 11/2010 | Brewer et al. | |
| 2012/0029571 A1 | 2/2012 | Schwab et al. | |

* cited by examiner

MANIFOLD HAVING ROTATABLE PORTS

CROSS REFERENCE

The present application claims priority to U.S. patent application Ser. No. 13/366,586, "Manifold Having Rotatable Ports" filed on Feb. 6, 2012, which is incorporated by reference in its entirety.

BACKGROUND OF THE INVENTION

Technical Field.

The present invention relates generally to multi-port medical devices. More particularly, the invention relates to a medical manifold having rotatable ports.

Background Information.

During the course of a medical or surgical treatment, a patient may be incapable of adequately breathing on his/her own. In order to ensure that a sufficient supply of oxygen is provided to the patient, the physician may initiate a period of artificial ventilation. Artificial ventilation is typically carried out by inserting an endotracheal tube into the trachea of the patient via the mouth or nose, a process referred to as intubation. A mechanical ventilator supplies oxygen through the endotracheal tube (ETT) to the patient's lungs.

During management of such patients, it may be desirable to coaxially insert one or more catheters, etc., into the patient's trachea through the ETT. Such devices may be positioned to carry out a medical procedure, or as a diagnostic tool. Examples of medical procedures include placement of a balloon-tipped catheter (e.g., an endobronchial blocker) for lung isolation, as well as other procedures such as jet ventilation, etc. Examples of diagnostic procedures include monitoring of bodily temperature, pressure, gas composition, etc. In such cases, the distal end of the catheter typically extends beyond the distal end of the ETT, and in many instances, is inserted into either the right or left mainstem bronchus. To ensure adequate placement, the position of the catheter is generally viewed through the endotracheal tube with an elongated viewing instrument, such as a fiberoptic bronchoscope.

A multi-port manifold may be engaged with the proximal end of the ETT to allow for simultaneous placement through the ETT of a plurality of different medical devices. Examples of such devices include a catheter (such as the endobronchial blocker catheter described above), various diagnostic tools, a bronchoscope, and a wire guide. Additionally, the manifold provides a conduit for ventilation of the patient. In some manifolds, each of these features is carried out through a separate port.

A distal port of the manifold is connected to the ETT. Another port is generally positioned in-line with the distal port, and with the lumen of the ETT. When introducing a bronchoscope into the airway, the bronchoscope is inserted through the in-line port, and extended through the distal port to ensure suitable visualization into the trachea. In some applications, a wire guide is inserted through a working channel of the bronchoscope, and directed into the desired right or left mainstem bronchus under visualization through the bronchoscope.

Once the wire guide is positioned in the desired region, the bronchoscope is removed from the in-line port. The catheter (e.g., an endobronchial blocker) is inserted over the wire guide in the in-line port, and advanced in the direction of the desired mainstem bronchus. The bronchoscope is then inserted through a side (angled) port to visualize the advancement of the catheter, and to verify that the catheter has entered the proper mainstem bronchus. Difficulties may be encountered when advancing a bronchoscope through a side port. A bronchoscope is typically a delicate instrument which has the ability to be tip deflected from the proximal end. However, the tip deflecting ability of such instruments can be impaired if the proximal end of the scope is at an acute angle with respect to the distal tip. In addition, when the bronchoscope is inserted through an angled port, the optics are generally not as suitable when compared to entry and advancement through an in-line port. In addition to the bronchoscope, other delicate and/or fragile instruments may be subject to impairment or damage if inserted through an angled port.

It would be desirable to overcome the problems encountered in the art by providing a manifold having multiple entry ports, wherein such ports are rotatable such that more than one port can be selectively axially aligned with the lumen of the ETT. It would further be desirable to provide rotatable entry ports wherein each port is arranged on the manifold in a manner such that each said port maintains access to the target site, to allow simultaneous passage of a respective medical device through each of said ports.

BRIEF SUMMARY

The present invention addresses the shortcomings of the prior art. In one form thereof, the invention comprises an airway manifold having a manifold body comprising an upper body portion and a lower body portion. The body portions are engaged such that the upper body portion is rotatable relative to the lower body portion, whereby a generally hollow interior space is defined thereby. The lower body portion has a port open to the interior space, and the upper body portion includes a plurality of ports open to the interior space. A first upper body port is axially alignable with the lower body port to define a substantially linear passageway therebetween when the upper body portion is at a first rotatable position relative to the lower body portion. A second upper body port is axially alignable with the lower body port to define a substantially linear passageway therebetween when the upper body portion is at a second rotatable position relative to the lower body portion.

In another form thereof, the invention comprises an airway system, wherein a manifold comprises an upper body and a lower body. The upper body and the lower body are engaged such that the upper body is rotatable relative to the lower body, and a generally hollow interior space is defined thereby. The lower body includes a first port and a second port, wherein each of the lower body ports is open to the interior space. The upper body includes a first port and a second port, wherein each of the upper body ports is open to the interior space. The upper body first port is axially alignable with the lower body first port to define a substantially linear passageway therebetween when the upper body is at a first rotatable position relative to the lower body. The upper body second port is axially alignable with the lower body first port to define a substantially linear passageway therebetween when the upper body is at a second rotatable position relative to the lower body. An airway tube is engaged with the lower body first port. A ventilator is engaged with the lower body second port. A viewing device is insertable through the upper body first port and the lower body first port when the upper body is at the first rotatable position relative to the lower body, and insertable through the upper body second port and the lower body first port when the upper body is at the second rotatable position relative to the lower body. A guide device is insertable through one of the first and second upper body ports and extendable therefrom through the airway tube.

In still another form, the invention comprises a method of introducing a medical device into a mainstem bronchus of a patient. A manifold is positioned at a proximal end of an airway tube. The manifold comprises an upper body and a lower body engaged such that the upper body is rotatable relative to the lower body, and such that a generally hollow interior space is defined thereby. The lower body includes a first port and a second port, each of which opens to the interior space. The upper body includes a first port and a second port, each of which opens to the interior space. The upper body first port is axially alignable with the lower body first port to define a substantially linear passageway therebetween when the upper body is at a first rotatable position relative to the lower body. The upper body second port is axially alignable with the lower body first port to define a substantially linear passageway therebetween when the upper body is at a second rotatable position relative to the lower body. The airway tube proximal end is positioned at the lower body first port, and the airway tube distal end extends into the trachea of the patient. The respective distal ends of a viewing device and a guide device are introduced through the upper body first port when the upper body is at the first rotatable position relative to the lower body, and the distal ends are advanced through the lower body first port and airway tube, and into the trachea. The distal ends are advanced toward a target mainstem bronchus, and the guide device distal end is advanced into the target bronchus under visualization from the viewing device. The viewing device is withdrawn through the upper body first port, and a position of the guide device is maintained along the first port and the target bronchus. The upper body is rotated to the second rotatable position relative to the lower body. The viewing device distal end is introduced through the upper body second port, and advanced through the lower body first port and airway tube toward the target mainstem bronchus. The distal end of the medical device is introduced through the upper body first port, and advanced toward the target bronchus. The medical device may comprise an endobronchial blocking device having an inflatable balloon at a distal end thereof, and the viewing device may comprise a bronchoscope.

BRIEF DESCRIPTION OF THE DRAWINGS

FIG. 11 is a view of an alternative embodiment wherein the manifold has three upper body ports.

DESCRIPTION OF THE PREFERRED EMBODIMENTS

Figure 1:
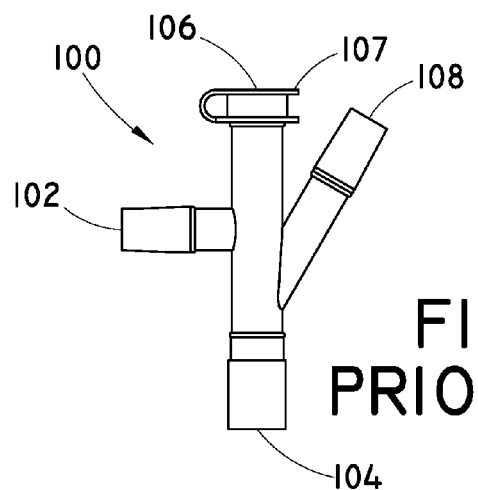
FIG. 1 is a side view of a prior art multi-port manifold.

For purposes of promoting an understanding of the present invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In the following discussion, the terms "proximal" and "distal" will be used to describe the opposing axial ends of the manifold, as well as the axial ends of various component features. The term "proximal" is used in its conventional sense to refer to the end of the manifold (or component) that is closest to the operator during use of the manifold. The term "distal" is used in its conventional sense to refer to the end of the manifold (or component) that is initially inserted into the patient, or that is closest to the patient during use.

FIG. 1 depicts an airway manifold 100 of a type known in the art. Manifold 100 includes a plurality of ports open to the interior of the manifold. A mechanical ventilation port 102 is configured for connection to a mechanical ventilator (not shown). An endotracheal tube connection port 104 is configured for connection to the proximal end of the endotracheal tube (not shown). A bronchoscope port 106 having an end cap 107 is positioned opposite to, and in-line with, the endotracheal tube connection port 104. An auxiliary port 108 is positioned at an angle with reference to the bronchoscope port. The auxiliary port may be configured to receive a wire guide, a catheter, or other treatment or diagnostic device. One example of a prior art manifold as shown in FIG. 1 is described in U.S. Pat. No. 6,086,529, incorporated by reference herein.

Figure 2:
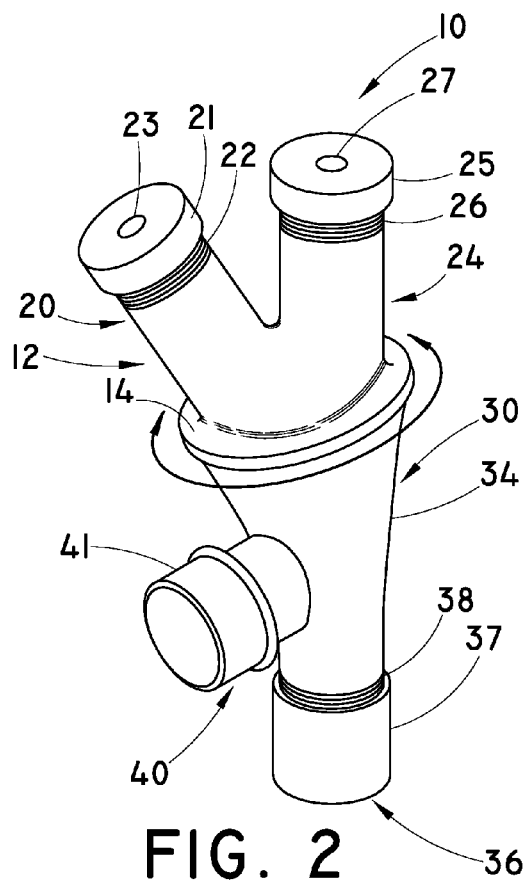
FIG. 2 is a perspective view of a manifold having rotational ports according to an embodiment of the present invention.
Figure 3:
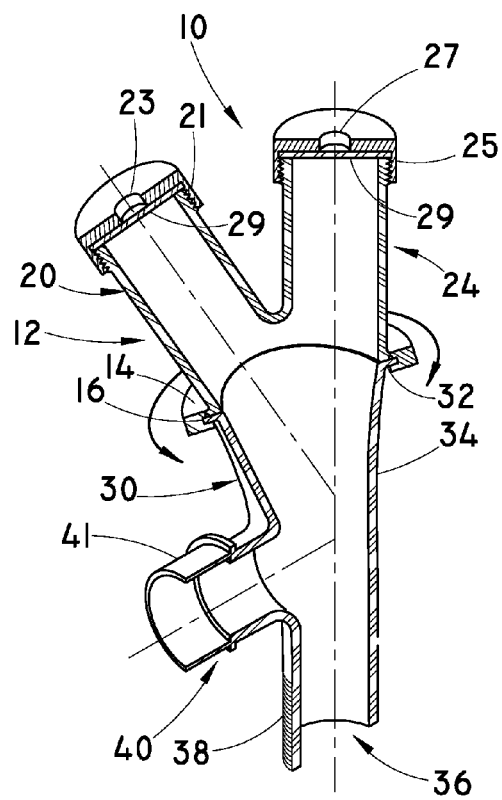
FIG. 3 is a longitudinal sectional view of the manifold shown in FIG. 2.
Figure 5:
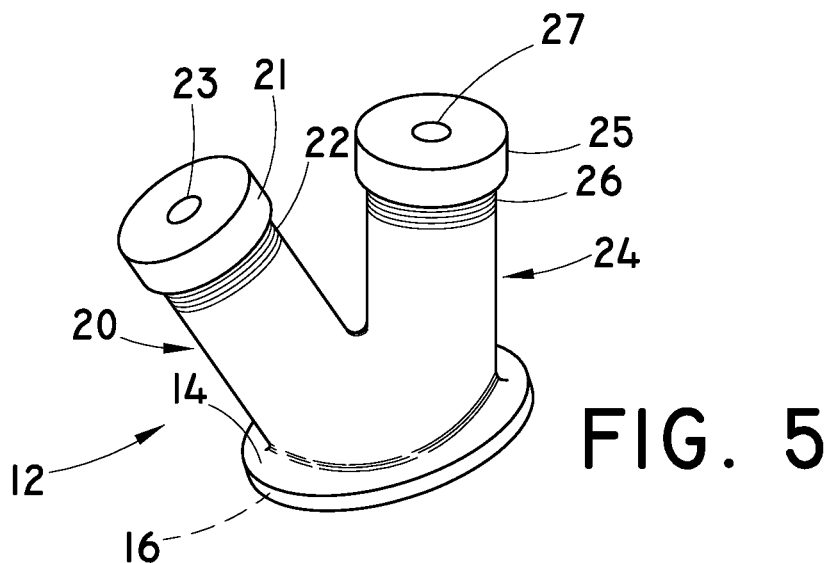
FIG. 5 is a view of the upper body portion of the manifold.
Figure 6:
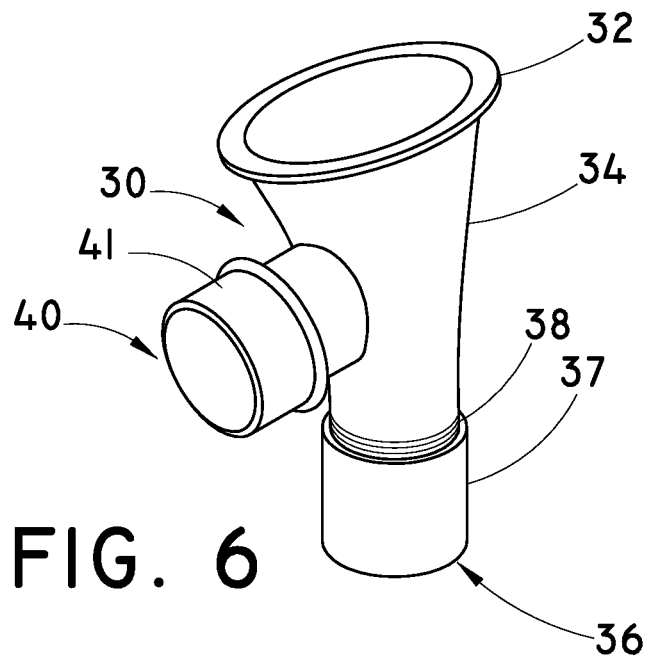
FIG. 6 is a view of the lower body portion of the manifold.

FIG. 2 is a perspective view of a manifold 10 according to an embodiment of the present invention. FIG. 3 is a longitudinal sectional view of the manifold of FIG. 2. As described herein, and as further shown in FIGS. 5 and 6, manifold 10 comprises an upper, or proximal portion 12 (FIG. 5), and a lower, or distal portion 30 (FIG. 6). Upper and lower portions 12, 30 are engaged to form manifold 10, and are configured to permit relative rotation between upper portion 12 and lower portion 30. In the non-limiting embodiment described in greater detail herein, manifold portions 12, 30 are rotatably engaged via a snap fit.

Upper portion 12 comprises an annular ledge 14, and includes ports 20, 24 extending in a proximal direction from ledge 14. As shown in FIG. 3, annular ledge 14 includes an internal slot 16 formed circumferentially therearound. Ports 20, 24 comprise respective generally tubular body members, and are spaced at an angle of, e.g., about 30-60 degrees relative to each other.

In the preferred embodiment shown, ports 20, 24 have a proximal end provided with external threads 22, 26, respectively. Respective end caps 21, 25 are sized and aligned for threaded connection with the external threads of ports 20, 24 via corresponding internal threads (not shown). An opening 23, 27 extends through each of the end caps and communicates with the hollow interior of manifold 10. In a preferred embodiment, a conventional valve member, such as check-flow valve 29 (FIG. 3) or a Tuohy valve, is provided internally of end cap 21, 25 in well-known fashion to establish a fluid-tight connection with a device extending through respective opening 23, 27.

Lower portion 30 includes a ring-like tab 32 at its upper, or proximal, end. In the embodiment shown, tab 32 is sized and configured to be received in internal slot 16 by conventional means, such as a snap fit. Tab 32 is dimensioned relative to slot 16 in a manner to inhibit disengagement of the respective upper and lower manifold portions 12, 30 during normal usage, but to permit relative rotation therebetween. Those skilled in the art will appreciate that other means for engagement of the respective upper and lower portions 12, 30 may be substituted, as long as such alternative means is structured to provide secure engagement between the respective upper and lower portions, while at the same time permitting relative rotation therebetween as described herein.

Figure 4:
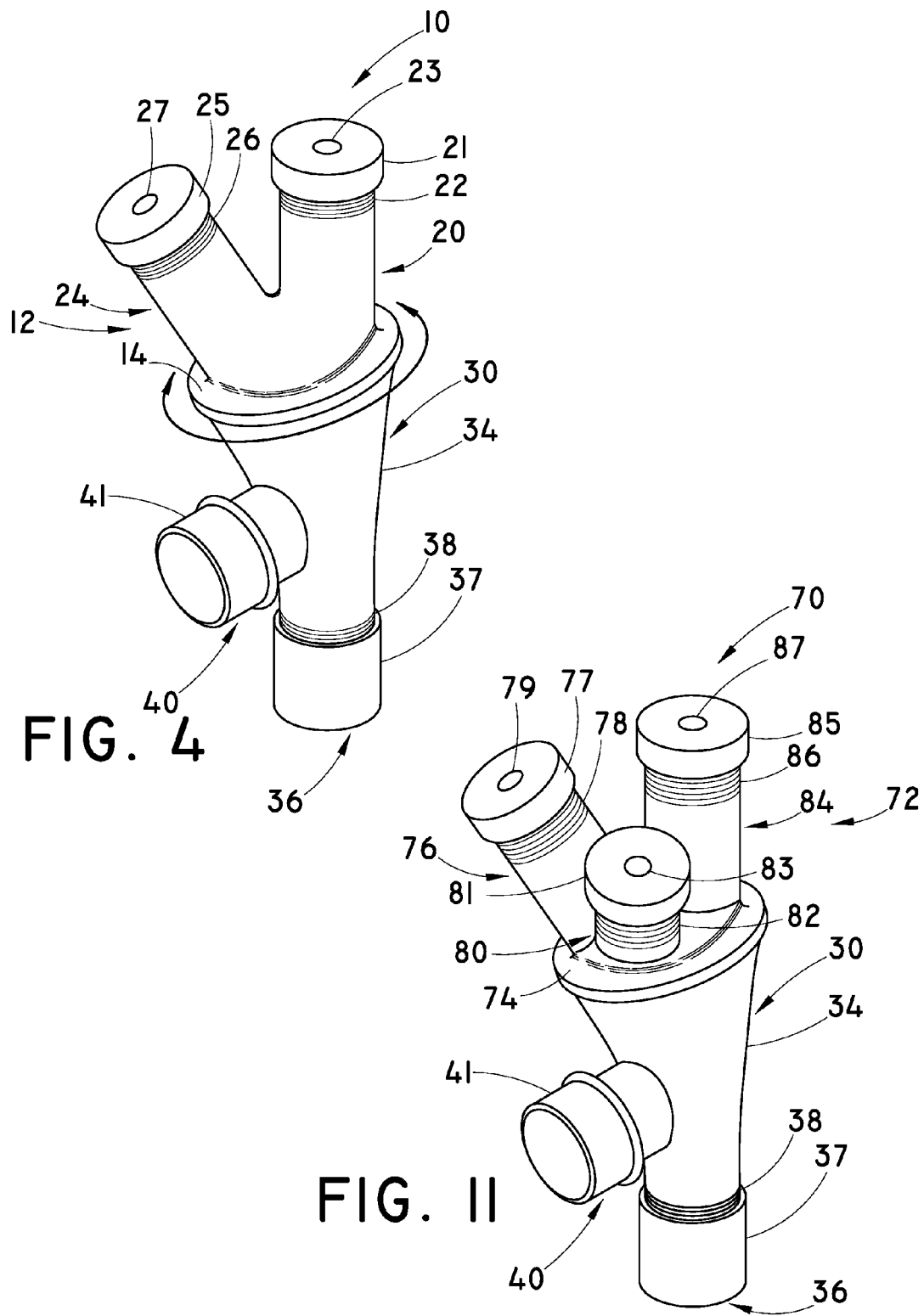
FIG. 4 is another perspective view of the manifold of FIG. 2, after a rotation of the upper body ports of the manifold.

As shown, e.g., in FIGS. 4 and 6, lower portion 30 comprises a generally elongated body 34. Elongated body 34 preferably tapers from the proximal end to at least a side port 40 that extends at an angle from elongated body 34. Port 40 may extend at an angle of about 90 degrees from body 34 as shown. Those skilled in the art will appreciate that although this angle is preferred, other angles, such as angles between about 30 and 60 degrees, may be substituted for the angle shown, as long as the position of port 40 does not functionally interfere with the remaining ports, as described herein. Port 40 may be configured to include a conventional 15 mm ventilator fitting portion 41 for connection to a mating fitting of a ventilation apparatus. Although port 40 is shown herein as having a fitting portion configured for engagement to a conventional 15 mm ventilator, this is not required. As a further alternative, port 40 may be configured for engagement with connectors of other configurations, for example, as a luer lock fitting for engagement with a corresponding connector of a jet ventilation device.

A distal port 36 is provided at the distal end of elongated body 34. Distal port 36 is configured for engagement with, e.g., a proximal end of an airway tube, such as an endotracheal tube or other breathing tube capable of supplying a ventilating fluid to the patient. In one embodiment, distal port 36 may be provided with external threads 38 that are sized and aligned for threaded connection with corresponding internal threads (not shown) of a connector 37. Connector 37 may be sized and configured for engagement in conventional manner with a proximal end of the endotracheal tube.

Upper and lower manifold portions 12, 30 are preferably formed of a generally rigid polymeric composition, such as a polycarbonate, polyamide (nylon), polyethylene, propylene, or other thermoplastic composition. Upper and lower portions 12, 30 may be formed and shaped by conventional processes, e.g., injection molding, insert molding, or conventional machining techniques. Those skilled in the art will appreciate that the compositions and forming techniques described herein are only intended to represent non-limiting examples, and that other known compositions and techniques may be suitable for a particular application.

An example illustrating the use of manifold 10 will now be provided. This example describes the use of manifold 10 for introducing an endobronchial blocker into a mainstem bronchus of a patient, in this case, into the right mainstem bronchus. Those skilled in the art will appreciate that this example is not intended to be limiting in any manner. Thus, the manifold may likewise be utilized for the introduction of other medical and diagnostic devices, and for introducing such devices at other target sites in the body of the patient.

Figure 7:
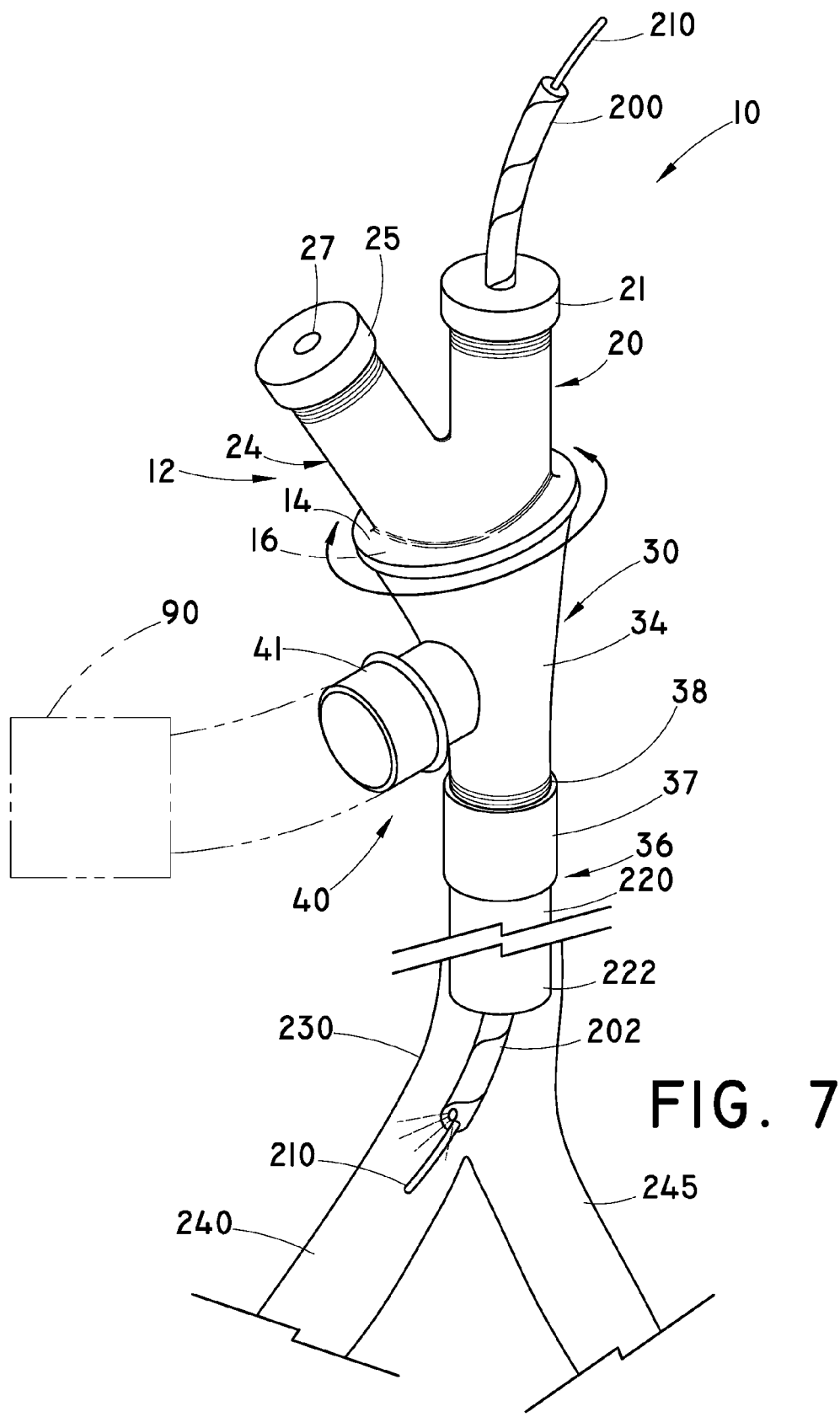
FIG. 7 is a view of the manifold connected to an endotracheal tube, wherein a first upper body port is axially in-line with a lower body port, and a bronchoscope extends through the axially aligned ports.

As described above, it is generally desirable to insert a device, such as a bronchoscope 200, through a proximal port of the manifold that is axially in-line with the distal port 36, and with the lumen of an endotracheal tube 220 that extends in a distal direction from distal port 36. This arrangement is shown in FIG. 7, wherein proximal port 20 is axially in-line with distal port 36 and endotracheal tube 220. Endotracheal tube 220 extends into the trachea 230 of the patient, in well-known manner. Only the distal portion of trachea 230 that branches into the right and left mainstem bronchus 240, 245, respectively, is shown in FIGS. 7-10. A ventilator 90 is schematically shown functionally engaged with port 40 in FIGS. 7-10. Ventilators, e.g., mechanical ventilators, jet ventilators, etc., are well known in the art, and those skilled in the art can readily select an appropriate ventilator for use herein. The remaining body portions of the patient are not shown, as they are not necessary for understanding the example described herein.

Upon insertion of bronchoscope 200 into port 20 as described, the distal end 202 of the bronchoscope extends beyond distal end 222 of the endotracheal tube, and is directed in a conventional manner to approach the selected right 240 or left 245 mainstem bronchus. In this example, the bronchoscope distal end 202 is deflected toward right mainstem bronchus 240 in well-known fashion, e.g., utilizing conventional articulating features of the bronchoscope.

A guide device, such as wire guide 210, is also inserted into port 20. Preferably, wire guide 210 is inserted via a lumen extending through bronchoscope 200. Under visualization provided by the bronchoscope, the distal end of wire guide 210 is advanced into right mainstem bronchus 240, as shown in FIG. 7. As described herein, it is desirable to obtain wire guide access to the selected bronchus, and to maintain such wire guide access during the period of time in which the medical device, e.g., the endobronchial blocker, is introduced and positioned in the selected mainstem bronchus. In addition, it is generally desirable to maintain wire guide access for a period of time thereafter, until it is confirmed that proper access has been achieved and that the device is functioning in a desired manner. By maintaining wire guide access to the target site, rapid reinsertion of a misplaced or non-functioning device, or rapid insertion of a replacement device, can be achieved if deemed necessary by the physician without the necessity to re-establish wire guide access to the target site, in this case, the right mainstem bronchus. Although referred to herein as a wire guide, those skilled in the art will appreciate that in some instances other thin-walled flexible devices, e.g., a thin-walled catheter or cannula, capable of carrying out the function of a wire guide as described herein may be substituted for a conventional wire guide.

Figure 8:
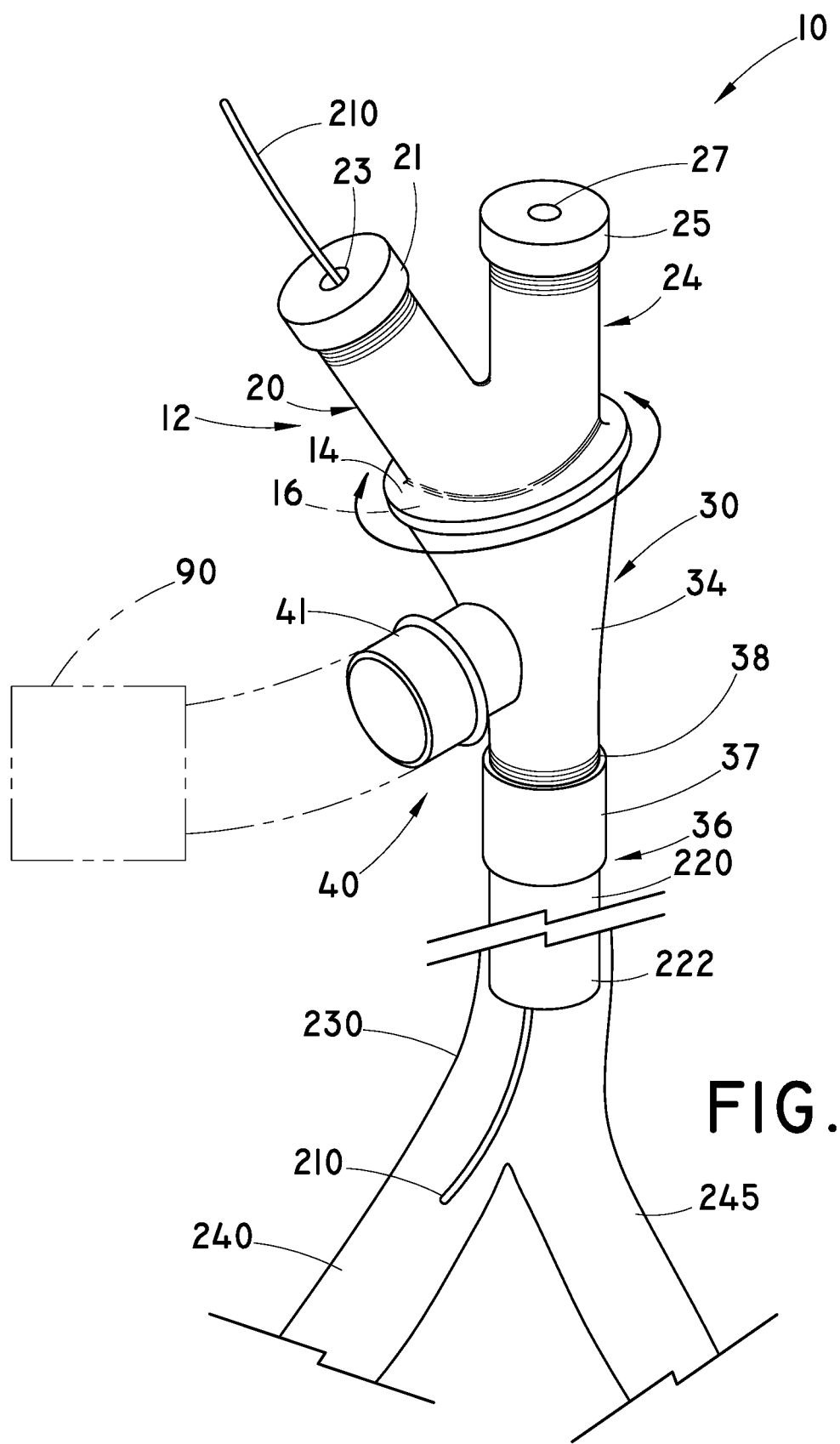
FIG. 8 is a view of the manifold connected to an endotracheal tube as in FIG. 7, wherein the bronchoscope has been withdrawn and the upper body ports have been rotated such that a second upper body port is axially in-line with the lower body port.

Once it is confirmed that the wire guide has accessed the right mainstem bronchus, the bronchoscope may be withdrawn over the wire guide, leaving the wire guide in place. At this time, the proximal ports 20, 24 of the upper manifold portion 12 may be rotated to a second position, as shown in FIG. 8. Following rotation of the ports, port 24 is now in-line with distal port 36 and the lumen of endotracheal tube 220.

Although wire guide 210 and port 20 are no longer in-line with the distal port 36, the wire guide continues to extend beyond the distal port and secure access into the mainstem bronchus 240.

At this time, bronchoscope 200 may be inserted into newly-aligned port 24 such that bronchoscope distal end 202 once again extends beyond distal end 222 of the endotracheal tube, and is directed toward right mainstem bronchus 240 as before. A medical device, such as endobronchial blocker 236, may be inserted into port 20 over wire guide 210. Endobronchial blocker 236 includes a blocker balloon 237 at its distal end.

Figure 9:
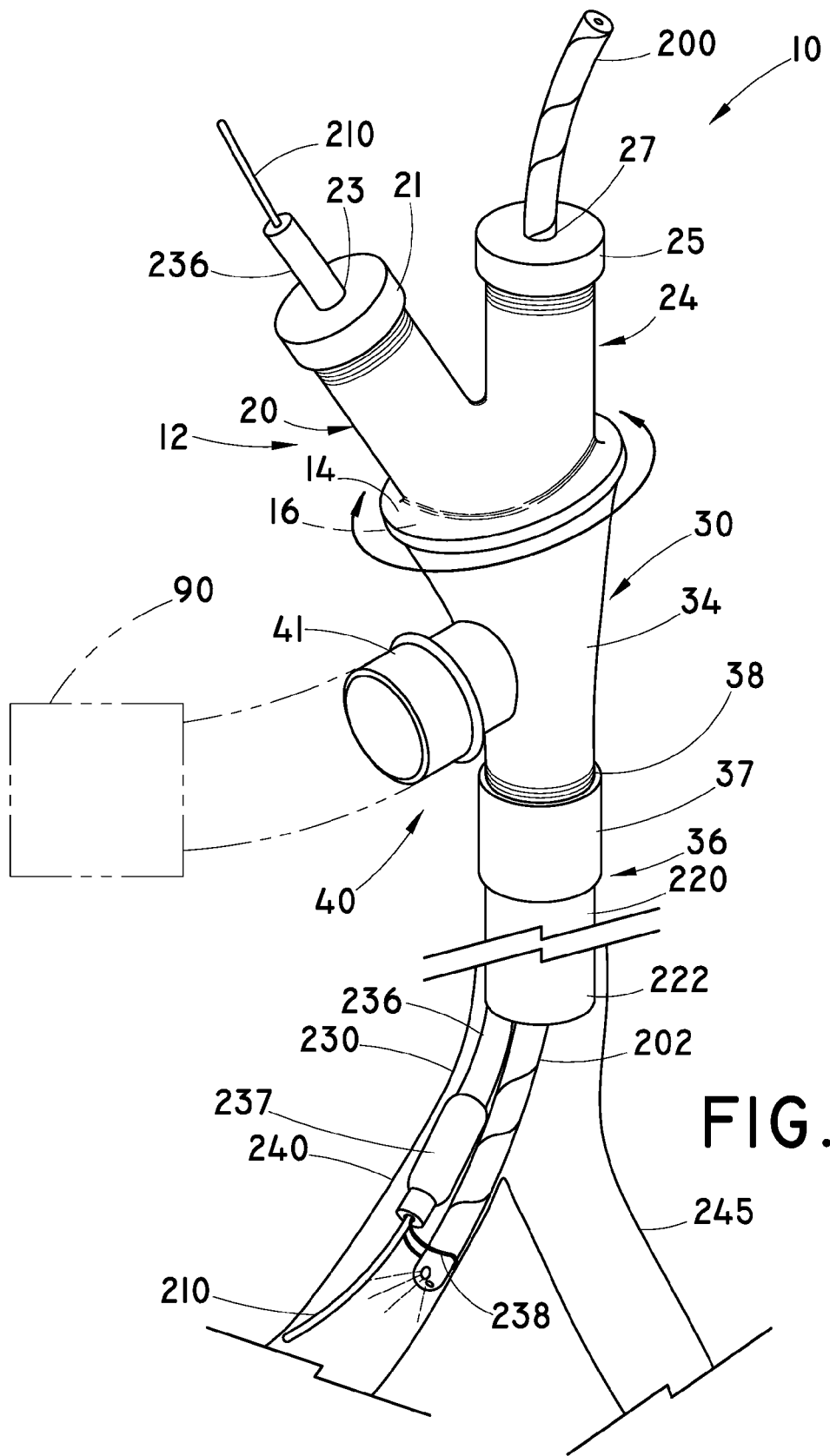
FIG. 9 is a view as in FIG. 8, wherein the bronchoscope has been inserted through the second upper body port, and an endobronchial blocking device has been inserted through the first upper body port.

Endobronchial blocker 236 is advanced in the right mainstem bronchus under visualization provided by the bronchoscope until the balloon is determined to be in a suitable location for inflation. If desired, blocker 236 can be provided with a distal loop 238 as described, e.g., in U.S. Pat. Nos. 5,904,648 and 7,578,295, both incorporated by reference herein. In this example, the distal loop receives the bronchoscope, so that as the bronchoscope advances into the right mainstem bronchus, the blocker may be advanced along with the bronchoscope. This is shown in FIG. 9.

Figure 10:
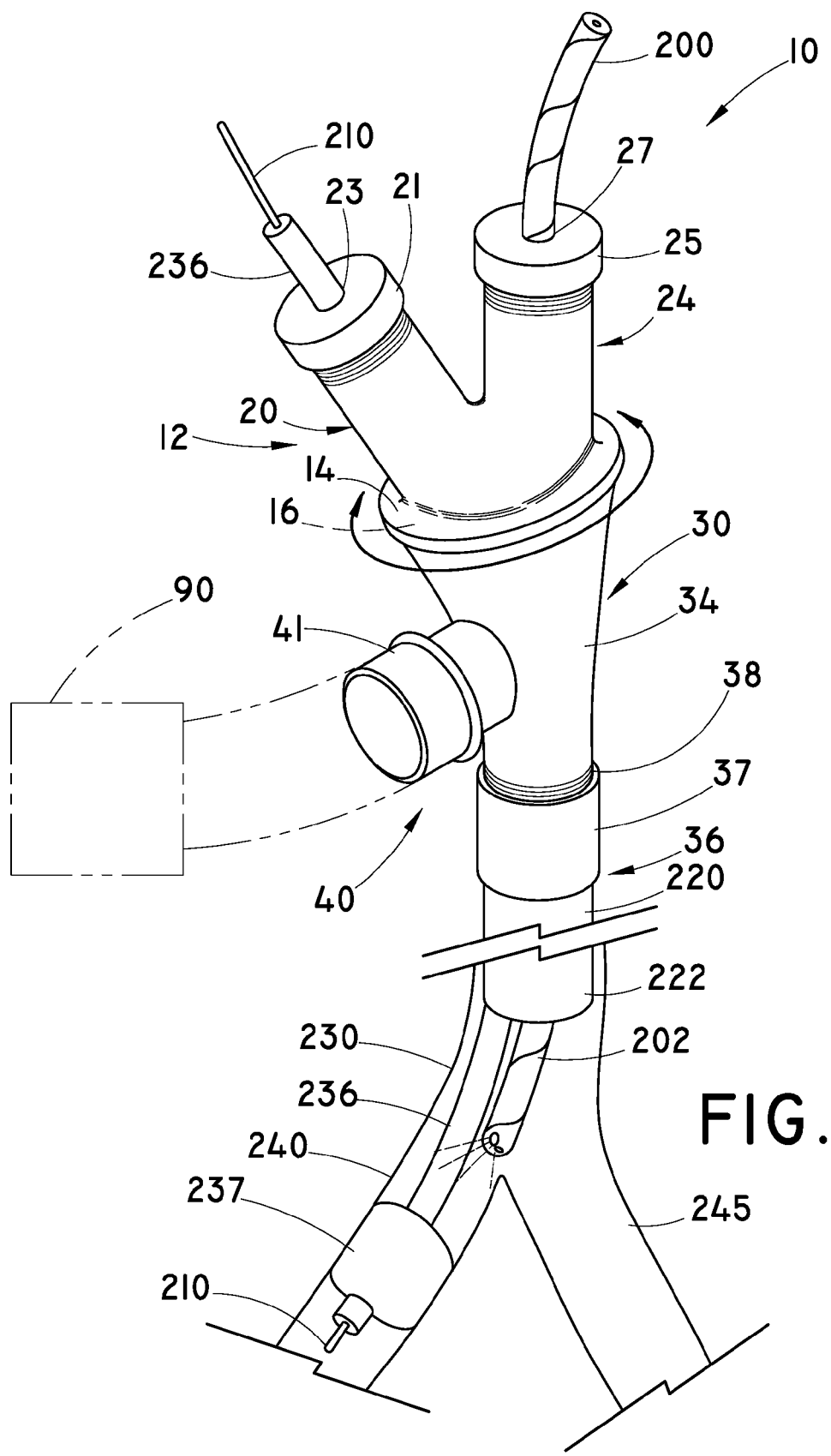
FIG. 10 is a view as in FIG. 9, wherein the balloon of the blocking device has been inflated in a target bronchus.

Once the distal end of the endobronchial blocker enters the bronchus, the bronchoscope may be partially withdrawn, e.g., approximately to the entry position of the bronchus or proximal of the entry point. The blocker may then be advanced to the desired position in the bronchus, under continued visualization by the bronchoscope. Once the balloon is deemed to be in a favorable position in the bronchus, the balloon is inflated, as shown in FIG. 10. Further discussion of the positioning of an endobronchial blocker in a desired mainstem bronchus is provided in the incorporated-by-reference patents.

Maintaining bronchoscopic visualization upon inflation of the balloon enables the physician to confirm proper placement, and inflation, of the balloon prior to removing the bronchoscope. Maintaining wire guide access to the target site enables the physician to quickly initiate remedial measures, such as replacement of the blocker, if deemed necessary, e.g., due to dislodgement or puncture of the balloon, etc. The rotatable features of the manifold enable the bronchoscope to be initially introduced, and re-introduced, through a port of the manifold that is axially in-line with the distal port, as described above.

FIG. 11 illustrates an alternate embodiment of a rotational manifold 70. Manifold lower portion 30 may be formed to have the same configuration as the lower portion in the preceding embodiment, and similar reference numbers are utilized to describe the features of the lower portion. In this embodiment, upper portion 72 has three upper ports 76, 80, 84 extending from annular ridge 74. Each of upper ports 76, 80, 84 may include a respective end cap 77, 81, 85, and may be provided with external threads 78, 82, 86, as described in the previous embodiment. Ports 76, 80, 84 may include respective openings 79, 83, 87 extending through each of the end caps.

In this embodiment, each of ports 76, 80, 84 communicates with the hollow interior of manifold 70. Upper manifold portion 72 is rotatable in the manner of upper manifold portion 12, such that a selected one of ports 76, 80, 84 may be axially in-line with port 36 at any particular time. As with the previous embodiments, a valve member (not shown) may be provided internally of the respective end cap to establish a fluid-tight connection. Those skilled in the art will appreciate that the presence of an additional port provides the opportunity to introduce additional devices, etc., to the target site without losing the access to that site provided by the wire guide.

It is therefore intended that the foregoing detailed description be regarded as illustrative rather than limiting, and that it be understood that it is the following claims, including all equivalents, that are intended to define the spirit and scope of this invention.

What is claimed is:

1. A method of introducing a medical device into a mainstem bronchus of a patient, comprising:

positioning a manifold at a proximal end of an airway tube, said manifold comprising an upper body and a lower body, said upper body and said lower body engaged such that said upper body is rotatable relative to said lower body, and such that a hollow interior space is defined thereby; said lower body including a lower body first port and a lower body second port, each of said lower body first port and said lower body second port open to said hollow interior space; said upper body including an upper body first port and an upper body second port, each of said upper body first port and said upper body second port continuously open to said hollow interior space; said upper body and said lower body defining a longitudinal axis passing through the hollow interior space and extending between the lower body first port and one of the upper body first port and the upper body second port, said upper body first port being aligned with the longitudinal axis to define a substantially linear passageway when said upper body is at a first rotatable position relative to said lower body, and said upper body second port being aligned with the longitudinal axis to define a substantially linear passageway when said upper body is at a second rotatable position relative to said lower body, said airway tube proximal end positioned at said lower body first port, said airway tube distal end extending into the trachea of the patient;

introducing a viewing device distal end and a guide device distal end through said upper body first port when said upper body is at said first rotatable position relative to said lower body and the upper body second port is angularly offset from the longitudinal axis, and advancing said distal ends through said lower body first port and airway tube, and into said trachea;

advancing said viewing device distal end and said guide device distal end toward a target mainstem bronchus, and advancing said guide device distal end into said target bronchus under visualization from said viewing device;

withdrawing said viewing device through said upper body first port, and maintaining a position of said guide device along said upper body first port and said target bronchus;

rotating said upper body to said second rotatable position relative to said lower body such that the upper body first port is angularly offset from the longitudinal axis;

introducing said viewing device distal end through said upper body second port, and advancing said viewing device distal end through said lower body first port and airway tube toward the target mainstem bronchus; and introducing a medical device distal end through said upper body first port, and advancing said medical device distal end toward said target bronchus.

2. The method of claim 1, wherein said medical device comprises an endobronchial blocking device having a balloon at a distal end of the endobronchial blocking device, and said viewing device comprises a bronchoscope, further comprising: advancing the distal end of said endobronchial blocking device into said target bronchus under visualization by the bronchoscope, with said balloon in an uninflated condition; confirming a placement of said uninflated balloon via said bronchoscope; and inflating said balloon.

3. The method of claim 2, further comprising: viewing a placement of said inflated balloon; and removing said bronchoscope through said upper body second port.

4. The method of claim 2, wherein said guide device comprises a wire guide, and wherein said endobronchial blocking device is advanced into said target bronchus over said wire guide.

5. The method of claim 1, wherein said medical device includes a loop at a distal portion thereof for receiving said viewing device, and wherein said viewing device is received in said loop, such that said medical device is advanced toward said target bronchus during advancement of said viewing device.

6. A method of operating an airway manifold, comprising: positioning a manifold at a proximal end of an airway tube, said manifold comprising an upper body and a lower body, said upper body and said lower body engaged such that said upper body is rotatable relative to said lower body, and such that a hollow interior space is defined thereby; said lower body including a lower body port open to said hollow interior space; said upper body including an upper body first port and an upper body second port, each of said upper body first port and said upper body second port continuously open to said hollow interior space; said upper body and said lower body defining a longitudinal axis passing through the hollow interior space and extending between the lower body port and one of the upper body first port and the upper body second port, wherein said upper body first port is aligned with the longitudinal axis to define a substantially linear passageway when said upper body is at a first rotatable position relative to said lower body, and said upper body second port is aligned with the longitudinal axis to define a substantially linear passageway when said upper body is at a second rotatable position relative to said lower body, said airway tube proximal end positioned at said lower body port, said airway tube distal end extending into a trachea of the patient; and
rotating said upper body from said first rotatable position to said second rotatable position relative to said lower body wherein the upper body first port is angularly offset from the longitudinal axis.

7. The method of claim 6, further comprising introducing a viewing device distal end and a guide device distal end through said upper body first port when said upper body is at said first rotatable position relative to said lower body and the upper body second port is angularly offset from the longitudinal axis, and advancing said distal ends through said lower body port and airway tube, and into said trachea.

8. The method of claim 7, further comprising advancing said viewing device distal end and said guide device distal end toward a target mainstem bronchus, and advancing said guide device distal end into said target bronchus under visualization from said viewing device.

9. The method of claim 8, further comprising withdrawing said viewing device through said upper body first port, and maintaining a position of said guide device along said upper body first port and said target bronchus.

10. The method of claim 9, further comprising introducing said viewing device distal end through said upper body second port after the upper body has been rotated to the second rotatable position relative to the lower body, and advancing said viewing device distal end through said lower body port and airway tube toward the target mainstem bronchus.

11. The method of claim 10, further comprising introducing a medical device distal end through said upper body first port, and advancing said medical device distal end toward said target bronchus.

12. The method of claim 11, wherein the medical device is advanced over said guide device.

13. The method of claim 12, wherein the medical device is an endobronchial blocking device.

14. The method of claim 13, further comprising withdrawing said endobronchial blocking device and advancing a second medical device through said upper body first port.

15. The method of claim 6, further comprising rotating the upper body to a third rotatable position relative to the lower body, wherein an upper body third port is aligned with the longitudinal axis to define a substantially linear passageway and the upper body first port and upper body second port are angularly offset from the longitudinal axis when said upper body is at the third rotatable position relative to said lower body.

16. The method of claim 6, further comprising coupling a ventilator to a lower body second port of the lower body.

17. A method of introducing a medical device through a manifold into a mainstem bronchus of a patient, comprising:
advancing a distal end of a viewing device and a distal end of a guide device through the manifold, the viewing device and guide device being introduced through an upper body first port in an upper body and being introduced into the patient through a lower body port in a lower body of the manifold, wherein the upper body and lower body of the manifold are rotatably coupled and the upper body first port and lower body port define a substantially linear passageway while the upper body is in a first rotatable position with respect to the lower body;
withdrawing the viewing device through the upper body first port;
rotating the upper body to a second rotatable position with respect to the lower body, wherein the lower body port and an upper body second port define the substantially linear passageway and the upper body first port is angularly offset from the linear passageway while the upper body is in the second rotatable position with respect to the lower body;
advancing the distal end of the viewing device through the upper body second port; and
advancing a distal end of a medical device to the mainstem bronchus through the upper body first port and over the guide device.

18. The method of claim 17, further comprising advancing the distal end of the guide device to the mainstem bronchus before withdrawing the viewing device through the upper body first port.

19. The method of claim 17, further comprising maintaining the position of the distal end of the guide device at the mainstem bronchus while rotating the upper body to the second rotatable position.

20. The method of claim 17, wherein the substantially linear passageway is defined by a longitudinal axis which extends along a center of the lower body port, wherein the lower body port is tubular.

* * * * *